US005702904A

United States Patent [19]
Makhlouf et al.

[11] Patent Number: 5,702,904
[45] Date of Patent: Dec. 30, 1997

[54] IMMUNOASSAY FOR IDENTIFYING ALCOHOLICS AND MONITORING ALCOHOL CONSUMPTION

[75] Inventors: Samar Makhlouf; Mark L. Pankow, both of Chicago; Byron E. Anderson, Norton Grove, all of Ill.; Pamela Bean, Los Angeles, Calif.

[73] Assignees: Immtech International, Inc.; Northwestern Univeristy, both of Evanston, Ill.

[21] Appl. No.: 272,852

[22] Filed: Jul. 8, 1994

Related U.S. Application Data

[63] Continuation of Ser. No. 765,169, Sep. 25, 1991, abandoned.

[51] Int. Cl.$^6$ ................................................. G01N 33/53
[52] U.S. Cl. .................... 435/7.1; 436/518; 436/523; 436/548; 436/811; 435/7.92; 435/70.21; 435/172.2; 435/240.27; 530/387.7; 530/388.25; 530/389.3; 530/391.1; 530/391.3; 424/139.1
[58] Field of Search .................... 436/518, 523, 436/548, 811; 435/7.92, 70.21, 172.2, 240.27, 810, 7.1; 530/387.9, 388.25, 389.3, 391.1, 391.3; 424/139.1

[56] References Cited

U.S. PATENT DOCUMENTS

| | | | |
|---|---|---|---|
| 4,571,382 | 2/1986 | Adachi | 435/7.9 |
| 4,626,355 | 12/1986 | Joustra et al. | 210/635 |
| 5,352,616 | 10/1994 | Sundrehagen | 436/501 |

FOREIGN PATENT DOCUMENTS

| | | |
|---|---|---|
| 043359 | 1/1982 | European Pat. Off. . |
| 134282 | 3/1985 | European Pat. Off. . |
| 166623 | 1/1986 | European Pat. Off. . |
| 2181840 | 4/1987 | United Kingdom . |
| WO 87/00289 | 1/1987 | WIPO . |

OTHER PUBLICATIONS

Bean et al., "Carbohydrate–Deficient Transferrin and False Positive Results for Alcohol Abuse in Primary Biliary Cirrhosis . . . ", Clin Chem 41(6):858–861 (1995).
Harlow, E. et al. *Antibodies A Laboratory Manual* 1988 Cold Spring Harbor pp. 72–76.
Stibler, H. & S. Borg, Alcoholism: Clinical and Experimental Research 10(1):61–64 Jan./Feb. 1986.
Payne, W.J. et al, Clinical Microbiology Reviews 1(3):313–329 Jul. 1988.
Anderson, G.J. et al The Journal of Laboratory and Clinical Medicine 107(1):59–65 Jan. 1986.
Yang, F. et al Proc. Natl. Acad. Sci 81:2752–56 May 1984.
Masutani et al., *Analytical Biochemistry*, 188, 149–54 (1990).
Wada et al., *Biochem. Biophys. Res. Commun.*, 189, 832–836 (1992).
Yamashita et al., *J. Biol. Chem.*, 268, 5783–89 (1993).
Jaeken et al., *Lancet*, 1398 (1987).
Stibler et al., *Arch. Dis. Childhood*, 65, 107–111 (1990).
Jaeken et al., *Genetics of Neurophysiatric Diseases*, 69–80 (1989).
Kristiansson et al., *Arch. Dis. Childhood*, 64, 71–76 (1989).
Jaeken et al., *Clin. Chim Acta*, 144, 245–247 (1984).
Behrens et al., *Alcholism: Clin. Exp. Res.*, 12, 427–431 (1988).
Blake et al. *Clin. Chem.*, 37, 5–13 (1991).
Cerven et al., *Uppsala J. Med. Sci.*, 86, 39–57 (1991).
Herbert et al., *Ann. N.Y. Acad. Sci.*, 252, 307–315 (1975).
Hillman et al., *Ann. N.Y. Acad. Sci.*, 252, 297–306 (1975).
Johansson et al., *Acta Med. Scand.*, 195, 273–277 (1974).
Lumeng et al., Review on Protein–Acetaldehyd Adducts as Biochemical Markers of Alcohol Consumption (in press).
MacGillirray et al., *J. Biol. Chem.*, 258, 3543–3553 (1983).
Marz et al., *Can. J. Biochem.*, 60, 624–630 (1982).
Orrego et al., *Lancet*, 1354–1356 (1979).
Orrego et al., *N. Eng. J. Med.*, 317, 1421–1427 (1987).
Petren et al., *Biochim. Biophys. Acta*, 994, 161–165 (1989).
Putman, in The Plasma Proteins: Structure, Function and Genetic Control, ed., Putman, F., Academic Press, NY, pp. 265–316 (1975).
Rollason et al., *Clin. Chim. Acta*, 39, 75–80 (1972).
Rosalki et al., *Clin. Chim. Acta*, 39, 41–47 (1972).
Schellenberg et al., *Drug Alcohol Depend.*, 19, 181–191 (1987).
Sixth Special Report to Congress on Alcohol and Health, Rockville, MD, Dept. Health and Human Services, NIAAA, 21–23 (DHHS Publication No. ADM 87–1519 (1979).
Stibler et al., *Acta Med Scand.*, 206, 275–281 (1979).
Stibler et al., *Alcoholism: Clin. Exp. Res.*, 10, 61–64 (1986).
Stibler et al., *Alcoholism: Clin. Exp. Res.*, 10, 535–544 (1986).
Stibler et al., *Alcoholism: Clin. Exp. Res.*, 11, 468–473 (1987).
Stibler et al., *Alcoholism: Clin. Exp. Res.*, 12, 450–453 (1988).
Stibler et al., *Alcohol*, 5, 393–398 (1988).
Storey et al., *Clin. Chem.*, 31, 1543–1545 (1986).
Storey et al., *Lancet*, 1292–1294 (1987).
van Eijk et al., *J. Clin. Chem. Clin. Biochem.*, 16, 557–560 (1978).
van Eijk et al., *J. Clin. Chem. Clin. Biochem.*, 18, 563–566 (1980).
van Eijk et al., *Clin. Chim. Acta*, 121, 201–216 (1982).
van Eijk et al., *Clin. Chim. Acta*, 165, 141–145 (1987).
West et al., *Ann. Int. Med.*, 100, 405–416 (1984).
Xin et al., *Gastroenterology*, 100, A812 (1991).

(List continued on next page.)

*Primary Examiner*—Carol A. Spiegel
*Attorney, Agent, or Firm*—Brinks Hofer Gilson & Lione

[57] ABSTRACT

The invention provides an antibody which reacts selectively with a transferrin homolog found in alcoholics but not in non-alcoholics. The invention also provides methods of making the antibody and hybridomas producing the antibody. Finally, the invention provides an immunoassay which utilizes the antibody to detect or quantitate the alcoholic transferrin homolog and a kit for an immunoassay which comprises a container of the antibody.

28 Claims, No Drawings

OTHER PUBLICATIONS

Yang et al., *Proc. Natl. Acad. Sci.*, 81, 2752–2756 (1984).
Anderson et al., *J. Lab. Clin. Med.*, 107, 59–65 (1986).
Cerven et al., *Upsala J. Med. Sci.*, 86, 39–53 (1981).
Heegaard et al., *Electrophoresis*, 10, 826–40 (1989).
Hradilek et al., *Brit. J. Haematol.*, 62, 21–30 (1986).
Kapur et al., *Brit. Med. J.*, 299, 427–31 (Aug. 12, 1989).
Kwoh–Gain et al., *Clin. Chem.*, 36/6, 841–45 (1990).
MacGillivray et al., *J. Biol. Chem.*, 258, 3543–53 (1983).
Markelonis et al., *J. Cell Biol.*, 100, 8–17 (1985).
Yang et al., *Proc. Natl. Acad. Sci. USA*, 81, 2752–56 (1984).
Beg et al., *Biochem. Intl.*, 17, 1135–42 (1988).
Hardy et al., *Anal. Biochem.*, 170, 54–62 (1988).
Hardy et al., *Proc. Natl. Acad. Sci. USA*, 85, 3289–93 (1989).
Pekelharing et al., *Anal. Biochem.*, 165, 320–26 (1987).
Riebe et al., *Electrophoresis*, 12, 287–43 (1991).
Sutton et al., *Biochem. J.*, 139, 163–68 (1974).
Sutton et al., *Eur. J. Biochem.*, 51, 43–48 (1975).
Townsend et al., *Anal. Biochem.*, 181, 001–008 (1989).

IMMUNOASSAY FOR IDENTIFYING ALCOHOLICS AND MONITORING ALCOHOL CONSUMPTION

This application is a continuation of application Ser. No. 07/765,169, filed Sep. 25, 1991 now abandoned.

FIELD OF THE INVENTION

The invention relates to an immunoassay useful for identifying alcoholics and monitoring alcohol consumption. In particular, the invention relates to the detection and quantitation of transferrin homologs found in alcoholics but not found in non-alcoholics.

BACKGROUND OF THE INVENTION

The magnitude of alcohol-related problems in the United States alone is enormous. Currently, over 200,000 deaths per year (1 of every 10 deaths) are attributable to alcoholism, and 20% of our total medical expenditures for hospital care are alcohol-related (West, L. T., Maxwell, D. S., Noble, E. P. and Solomon, D. H., *Ann. Int. Med.*, 100, 405–416, 1984). In the United States, the annual cost of lost productivity and health care expenses related to alcoholism is estimated to be $117 billion (Sixth Special Report to Congress on Alcohol and Health, Rockville, Md., Dept. Health and Human Services, NIAAA, 1987:21–23. (DHHS Publication No. ADM 87-1519)). Approximately 18 million Americans are considered to be alcohol dependent.

Current tests used to diagnose alcoholism are not specific for the condition. Hence, multiple tests are performed and evaluated to arrive at a diagnosis of alcoholism. Severity indices based on multiple tests are used to monitor treatment of alcohol-related liver disease (Blake, J. and Orrego, H., *Clin. Chem.*, 37, 5–13, 1991). In alcoholism, the serum gamma-glutamyl transferase is often elevated (Rollason, J., Pincherly, G. and Robinson, D., *Clin. Chim. Acta*, 39, 75–80, 1972; Rosalki, S. and Rau, D., *Clin. Chim. Acta*, 39, 41–47, 1972). Elevations also have been observed in alpha-lipoprotein (Johansson, B. and Medhus, A., *Acta Med. Scand.*, 195, 273–277, 1974) and serum iron (Hillman, R., *Ann. N.Y. Acad. Sci.*, 252, 297–306, 1975; Herbert, V. and Tisman, G., *Ann. N.Y. Acad. Sci.*, 252, 307–315, 1975). Because alcoholics often have various forms of anemias and blood clotting disorders, other abnormal laboratory results may include elevated prothrombin time and thrombocytopenia (Gitlow, S. and Peyser, H. S. in "Alcoholism, A Practical Treatment Guide," Grune and Stratton, Inc., Philadelphia, Pa. p.218, 1988). Blake and Orrego recently discussed the various indices of prognostic significance to the treatment of alcohol-related liver disease and concluded that functional variables (mainly blood tests) are more important than histological abnormalities (Blake, J. and Orrego, H., *Clin. Chem.*, 37, 5–13, 1991). Regardless, a high level of clinical expertise is necessary in evaluating clinical data from alcoholic patients.

Assessment of the level alcohol intake is very important because of its effects on treatment outcome (Blake, J. and Orrego, H., *Clin. Chem.*, 37, 5–13, 1991; Orrego, H., Blake, J. G., Blendis, L. M., Compton, K. V. and Israel, Y., *N. Eng. J. Med.*, 317, 1421–1427, 1987). However, patients, especially alcoholics, are unreliable in reporting alcohol consumption (Orrego, H., Blake, J. G., Blendis, L. M., Kapur, B. M. and Israel, Y., *Lancet*, 1354–1356, 1979). Thus, a biochemical test which correlates with prolonged excessive alcohol consumption would be very useful. For example, Stibler and co-workers (Stibler, H., Borg, S. and Alluglande, C., *Acta Med Scand.*, 206, 275–281, 1979) have found that higher isoelectric point (pI) isoforms of transferrin are elevated in 81% of patients who ingested 60 g or more of ethanol every day for a week or more, and that the higher isoforms return to normal levels if the patient abstains for 10 or more days.

Transferrin is the major iron transport glycoprotein of the blood with a molecular weight of 79,500 Daltons. The protein portion consists of a single polypeptide chain with two homologous halves, each having an iron binding site (MacGillirray, R. T. A., Mendez, E., Shewale, J. G., Sinha, S. K., Lineback-Zing, J. and Brew, K., *J. Biol. Chem.*, 258, 3543–3553, 1983). The carbohydrate chains of the molecule are attached to asparagine (Asn) residues at the 413 and 611 positions in the C-terminal domain of the glycoprotein (MacGillirray, R. T. A., Mendez, E., Shewale, J. G., Sinha, S. K., Lineback-Zing, J. and Brew, K., *J. Biol. Chem.*, 258, 3543–3553, 1983).

Five isoforms of the molecule have been detected, based on the isoelectric focusing differences which are thought to reflect different amounts of sialic acids attached to the ends of the carbohydrate chains. The main isoform has a pI of 5.4 and has four sialic acid terminals per transferrin molecule (van Eijk, H. G., van Noort, W. L., de Jong, G. and Koster, J. F., *Clin. Chim. Acta*, 165, 141–145, 1987; Petren, S. and Vesterberg, O., *Biochim. Biophys. Acta*, 994, 161–165, 1989). Small amounts of transferrins which focus at the higher pI values of 5.6 and 5.7 are present in normal serum and are thought to represent transferrins missing one or two sialic acid terminals, respectively. These isoforms are referred to as trisialo- and disialo-transferrin, respectively (Marz, L., Hatton, M. W. C., Berry, L. R. and Regoerzi, E., *Can. J. Biochem.*, 60, 624–630, 1982). The isoform which is significantly increased in serum from alcoholics focuses at a pI of 5.7 and is widely known as "disialo-transferrin." Additionally, alcoholic sera may contain trace amounts of pI 5.8 and 5.9 transferrin isoforms which are thought to have one and no sialic acid terminals, respectively. These isoforms are referred to as the monosialo- and asialo-transferrins, respectively. Approximately 80% of transferrin has oligosaccharide chains believed to be arranged in two "antennae" and are referred to as the biantennary types. Another 15% of transferrin is the tri-antennary form, and the remaining 5% of transferrin is the tetra-antennary form (Marz, L., Hatton, M. W. C., Berry, L. R. and Regoerzi, E., *Can. J. Biochem.*, 60, 624–630, 1982). The tri- and tetra-antennary oligosaccharide forms of transferrin are thought to be represented at pIs of about 5.2–5.3.

The transferrin isoforms described above were detected using isoelectric focusing with a pH gradient of 3–10 or 3–11. When a narrower pH range (5–7 or 4–8) is used, additional isoforms of transferrin are found between pIs of 5.5 and 6.0 (van Eijk, H. G., van Noort, W. L. and van der Heul, C., *J. Clin. Chem. Clin. Biochem.*, 18, 563–566, 1980; van Eijk, H. G., van Noort, W. L., Kroos, M. J. and van der Heul, C., *Clin. Chim. Acta*, 121, 201–216, 1982; van Eijk, H. G., van Noort, W. L. and van der Heul, C., *J. Clin. Chem. Clin. Biochem.*, 16, 557–560, 1970). These additional isoforms have been isolated and characterized as binding different amounts of iron. There is one di-ferric form, two mono-ferric forms, and one form of transferrin lacking any bound iron (no-iron). Conditions have been employed to increase iron "saturation" but do not completely saturate the two iron binding sites. Accordingly, although "saturating" conditions have been used by workers in characterizing and quantitating the pI 5.7 isoform, there is still some question as to the amounts of mono-ferric and no-iron forms of transferrin that may co-migrate with transferrin isoforms lacking acid terminals.

The amounts of the pI 5.7 isoform in alcoholic sera vary with the method of detection. Using ultra thin polyacrylamide gel separation followed by quantitative densitometry, Schillenberg and Weill (Schnelenberg, F. and Weill, J., *Drug Alcohol Depend.*, 19, 181–191, 1987) found that the pI 5.7 isoform of transferrin represented 1.4–3.7% of the total transferrin in non-alcoholics, and that males and females had mean levels of 3.0% and 2.4%, respectively. In alcoholics the pI 5.7 isoform constituted 2.5–16.4% of the total transferrin; males and females had mean levels of 6.4% and 7.4%, respectively. Xin et al. used a similar method of detecting the transferrin isoforms with anti-transferrin antibody (Xin, Y., Lasker, J. M., Rosman, A. S. and Lieber, C. S., *Gastroenterology*, 100, A812, 1991). Xin et al. found that alcoholic sera contained carbohydrate-deficient transferrin (CDT) in amounts of 145±43 mg/l (with liver disease) and 117±30 mg/l (without liver disease). CDT levels in abstainers or non-alcoholics (with or without liver disease) ranged between 68 and 86 mg/l. When an abnormal value is defined as the sum of the control group's mean plus two standard deviations, the CDT was abnormal in about 80% of alcoholic patients. Unfortunately, significant amounts (68–86 mg/l) of CDT or pI 5.7–5.9 isoforms were also found in the control groups.

Storey et al. (Storey, E. L., Mack, U., Powell, L. W. and Holliday, J. W., *Clin. Chem.*, 31, 1543–1545, 1986; Storey, E. L., Anderson, G. J., Mack, U., Powell, L. V. and Holliday, J. W., *Lancet*, 1292–1294, 1987) measured the "partially desialylated" transferrin fraction (or higher pI isoforms) using chromatofocusing to separate the isoforms based on expected charge differences. The eluted transferrin was identified by a radioimmunoassay (RIA) for transferrin. The maximum amount of the higher pI transfertin isoform in non-alcoholic sera was 1.5%, whereas 18 of 20 alcoholic sera contained 2–13% of the alcoholic isoform.

Stibler et al. (Stibler, H., Borg, S. and Joustra, M., *Alcohol Clin. Exp. Res.*, 10, 534–544, 1986) developed another method which utilizes small disposable anion exchange columns. First, iron is added to patient sera in an amount insufficient to saturate transferrin. Then the sera diluted in piperazine buffer (pH 5.65) are passed through the columns. The eluates containing pI 5.7 and any higher pI isoforms were then tested for transferrin using a double antibody RIA. Levels of these abnormal isoforms were reported as the amounts of carbohydrate deficient transferrin (CDT) in mg/l of serum. Total abstainers had a CDT range of 27–71 mg/l and a mean of 50 mg/l. Normal (moderate) alcohol consumers had a CDT range of 26–74 mg/l and a mean of 53 mg/l. Alcoholics were found to have higher CDT values, with a range of 34–372 mg/l and a mean of 138 mg/l. These mean values are very close to those obtained by Xin et al. (Xin, Y., Lasker, J. M., Rosman, A. S. and Lieber, C. S., *Gastroenterology*, 100, A812, 1991) using isoelectric focusing followed by isoform quantitation by Western blot with anti-human transferrin. The normal "pI 5.7" isoform values were thought to be due to the presence of mono- or no-ferric forms of transferrin.

A clinical evaluation of the microanion exchange method by Stibler et al. (Stibler, H., Borg, S. and Joustra, M., *Alcohol Clin. Exp. Res.*, 10, 534–544, 1986) indicated that the alcoholic patients could clearly be separated from abstainers and moderate consumers with a specificity of 100% and a sensitivity of 91%. The CDT values correlated with alcoholic consumption during the preceding month. In abstaining alcoholics, the values declined with a mean half-life of 17 days. Nevertheless, this test has shortcomings because the transferrin isoforms must first be separated based by isoelectric focusing. Also, the assay will not work correctly if the pH of the piperazine buffer differs by only 0.05 pH units from a pH of 5.65. And finally, the separations were found to be very sensitive to ionic additives such as common anticoagulants EDTA and heparin.

The genetic B- and D-variants of transferrin are rare in most populations, but the D variant is found in about 10% of American Blacks and certain Asian and South American populations (Putman, F., in *The Plasma Proteins: Structure, Function and Genetic Control*, ed., Putman, F., Academic Press, New York, pp. 265–316, 1975). This can result in false-positive results because the pIs of the B- and D-variants are close to that of the alcoholic pI 5.7 isoform (Behrens, U. J., Warner, T. M., Braly, L. F., Schaffner, F. and Lieber, C. S., *Alcoholism: Clin. Ext. Res.*, 12, 427–431, 1988; Stibler, H. Borg, S. and Beckman, G., *Alcoholism: Clin. Exp. Res.*, 12, 450–453, 1988).

Regardless of the possible shortcomings of published assays for the higher pI isoforms of transferrins, the utility and importance of the assays have been established. Stibler's laboratory (Stibler, H. and Hultcrantz, R., *Alcoholism: Clin. Exp. Res.*, 11, 468–473, 1987; Stibler, H., Dahlgren, L. and Borg, S., *Alcohol*, 5, 393–398, 1988) has also shown that the higher CDT levels in alcoholics are independent of previous or associated liver disorders (and non-alcoholic liver disease patients do not exhibit the high CDT levels), and that determination of CDT levels may provide an early, objective diagnosis for women in early stages of alcoholism.

Recently, a new genetic syndrome characterized by a severe neurologic deficit and carbohydrate deficient serum glycoproteins and high levels of CDT (about 25% of total transferrin) has been described by Stibler and colleagues (Jaeken, J., Eggermount, E. and Stibler, H., *Lancet*, 1398, 1987; Stibler, H. and Jaeken, J., *Arch. Dis. Childhood*, 65, 107–111, 1990; Jaeken, J. and Stibler, H., in *Genetics of Neurophysiatric Diseases*, Wetterburg, L., ed., Wenner-Gren Int. Symp. Series, Vol. 51, Macmillan Press, London, pp. 69–80, 1989), Kristiansson et al. (Kristiansson, B., Andersson, M., Tonnby, B. and Hagberg, B., *Arch. Dis. Childhood*, 64, 71–76, 1989) and Jaeken et al. (Jaeken, J., van Eijk, H. G., van der Heul, C., Corbeel, L., Eeckels, R. and Eggermount, E., *Clin. Chim. Acta*, 144, 245–247, 1984). Based on carbohydrate compositions of the CDT and certain glycosyl-transferase activities from these children, Jaeken and Stibler concluded that the defect may be in either GlcNAc-transferase I or II, which attach GlcNAc to the terminal trisaccharide sequences of N-linked oligosaccharides. A defect in the GlcNAc-transferases would yield glycoproteins with mannose-terminals on the oligosaccharide chains. It is not yet known if these children's CDT differs from that of alcoholics or if the abnormal CDT's differ in the same way from normal transferrin; however, Stibler and Borg's analyses of alcoholic transferrin indicated a reduced content of terminal trisaccharide portions of the oligosaccharide chains (Stibler, H. and Borg., J. *Alcohol Clin. Exp. Res.*, 10, 61–64, 1986). Similar data regarding the carbohydrate components of the children's pI 5.7 isoform have yet to be reported.

The CDT species migrating to pIs of 5.6, 5.7, 5.8 and 5.9 can be artificially generated by incubating the common pI 5.4 isoform of transferrin with neuraminidase enzyme for different time periods. (See Petren, S. and Vesterberg, O., *Biochim. Biophys. Acta*, 994, 161–165, 1989; Marz, L., Hatton, M. W. C., Berry, L. R. and Regoerzi, E., *Can. J.*

Biochem., 60, 624–630, 1982; van Eijk, H. G., van Noort, W. L., Kroos, M. J. and van der Heul, C., Clin. Chim. Acta, 121, 201–216, 1982). If the CDTs represent formerly penta- to mono-sialyl-transferrins, and transferrin devoid of any sialic acid, then the new transferrin species should have terminal galactose moieties. In 1981, Cerven et al. (Cerven, C., Stibler, H. and Borg, S., Uppsala J. Med. Sci., 86, 39–57, 1991; Cerven, C., European patent application number EP 0043359 A2, 1982), described a method for quantitating differences between alcoholic and normal transferrins in serum specimens. Anti-human transferrin was used to capture transferrin from serum, after which the transferrin was reacted with $^{125}$I-labeled *Crotalaria juncea*, a lectin which binds to galactose. Joustra et al. (U.S. Pat. No. 4,626,355) report that the Cerven et al. method does not show a significant difference between alcoholic and non-alcoholic sera and that high backgrounds were encountered.

As discussed above, the isoelectric focusing followed by quantitative densitometry (either after protein staining or detection with anti-human transferrin antibody), and the micro-anion exchange column methods yield clear distinctions for differentiating normal and alcoholic CDT quantities. These assays are useful but inconvenient, being both time consuming and labor intensive. Isoelectric focusing followed by staining is an involved procedure; the micro-anion column technique requires a separate disposable column for each sample followed by RIA analysis of the eluates. Also, as mentioned above, some of the CDTs quantitated by those methods are probably mono-ferric and no-ferric forms of transferrin and accounts for the presence of CDT in normal sera. Also, the D-variants of transferrin which are found in about 10% of certain racial/ethnic populations also will give unacceptably high rates of false-positive results.

Lumeng and Lin (Lumeng, L. and Lin, R. C., Review on Protein-Acetaldehyde Adducts as Biochemical Markers of Alcohol Consumption, in press) have recently summarized alcoholism markers which are currently available and in development, particularly markers produced by ethanol metabolism. They concluded that CDT serum quantitation is currently the most reliable test, whereas all other markers lack specificity or sensitivity. Measurements of ethanol metabolic products have limitations due to genetic variations of alcohol dehydrogenase (ADH) and aldehyde dehydrogenase (ADLH), environmental factors and liver injury. Quantitation of acetaldehyde adducts (AA) of blood proteins (in particular AA-hemoglobin) has shown some promise but also suffers from lack of accuracy of measurements and specificity of alcoholism-relatedness. A recent test for AA-albumin using antibody generated to the reduced AA shows promise.

SUMMARY OF THE INVENTION

The invention provides an antibody which reacts selectively with a transferrin homolog found in alcoholics but not in non-alcoholics. The antibody may be a polyclonal or monoclonal antibody.

The invention also provides a method of making the antibody which comprises immunizing an animal with an immunogen comprising the alcoholic transferrin homolog, or a portion thereof sufficient to elicit the desired antibody. When monoclonal antibodies are desired, the method comprises the additional steps of fusing immunoglobulin-producing cells from the immunized animal with immortal cells and selecting for hybridomas producing the desired antibody. The selected hybridoma cells are either cultured to produce the monoclonal antibody or injected into an animal so as to produce ascites fluid which contains the monoclonal antibody. The invention also provides the hybridomas which produce the monoclonal antibody.

Finally, the invention provides an immunoassay and a kit for performing the immunoassay. The immunoassay includes the following steps: 1) providing a sample of a body fluid containing transferrin; 2) contacting the sample with an antibody which reacts selectively with a transferrin homolog found in alcoholics but not found in non-alcoholics; and 3) detecting or quantitating any of the alcoholic transferrin homolog present in the sample. The kit includes a container of an antibody which reacts selectively with a transferrin homolog found in alcoholics but not found in non-alcoholics.

The immunoassay of the invention allows for the identification of alcoholics and for the monitoring of alcohol consumption. It is a much more rapid and easy to use assay than prior art assays for monitoring alcoholics and alcohol consumption. It is also more reliable and accurate than prior art assays since it detects transferrin homologs found only in the body fluids of alcoholics. In particular, prior art methods could not accurately assess alcoholism in certain individuals due the presence in non-alcoholics of a substantial amount of the pI isoforms associated with alcoholism. This difficulty is overcome by the present method.

DETAILED DESCRIPTION OF THE PRESENTLY PREFERRED EMBODIMENTS

The invention provides an antibody which reacts selectively with a transferrin homolog found in alcoholics but not found in non-alcoholics. An "alcoholic" is defined herein to be an individual who ingests 60 grams or more of ethanol per day for a period of one week or more. A "non-alcoholic" is an individual who does not fit the definition of an alcoholic. Non-alcoholics include those who do not drink or who drink more moderately than set forth above. Non-alcoholics also include those who, although having a history of alcoholism, have abstained from alcohol for a period of at least ten days.

As used herein, "homolog" refers to the various chemical forms in which transferrin may exist. For instance, transferrin homologs include trisialo-, disialo- and asialo-transferrins and the diferric, two monoferric and no iron forms of transferrin. Transferrin homologs are distinguishable from the "pI isoforms" described in the prior art because the pI isoforms are defined by their behavior in isoelectric focusing, whereas the homologs are defined in terms of their chemical composition. Thus, the pI isoforms may consist of one or more homologs.

As used herein, "alcoholic transferrin homolog" refers to a transferrin homolog found in alcoholics but not found in non-alcoholics. A "normal transferrin homolog" is a transferrin homolog found in non-alcoholics which may also be found in alcoholics. The chemical differences between alcoholic and normal transferrin homologs have not yet been completely characterized. However, it has been determined that alcoholic transferrin homologs exist which appear to lack one (or most of one) of the two bi-antennary carbohydrate chains normally present on transferrin (see below).

The antibodies of the invention react selectively with an alcoholic transferrin homolog. By "selectively" it is meant that the antibody exhibits statistically significantly greater reactivity with the alcoholic transferrin homolog than with normal transferrin homologs.

To prepare the antibodies of the invention, an animal may be immunized with an immunogen comprising the alcoholic transferrin homolog. Thus, the immunogen can be a mixture of transferrin homologs, including at least one alcoholic transferrin homolog, isolated from a body fluid of an alcoholic. For instance, the immunogen could be that population of transferrin homologs isolated from the sera of alcoholics by affinity chromatography using an anti-transferrin antibody reactive with all transferrin homologs. Alternatively, the immunogen could be the population of transferrin homologs isolated by isoelectric focusing having a pI of 5.7. As discussed in the Background section, the level of pI 5.7 transferrins has been shown to be increased substantially in alcoholics. Other pI isoforms found in alcoholic sera, but not in normal sera, can also be used as immunogens.

The immunogen may also be a portion of an alcoholic transferrin-homolog sufficient to elicit the desired antibody. For instance, it has been determined that alcoholic transferrin homologs exist which appear to lack one (or most of one) of the two bi-antennary carbohydrate chains normally present on transferrin (see Example 1). With all or most of one of the chains missing, protein regions would be exposed on the alcoholic transferrin homologs which are not exposed on normal transferrin homologs, and antibodies according to the invention include antibodies directed to the regions exposed when one of the two bi-antennary oligosaccharide chains is missing. Suitable immunogens for the production of such antibodies are peptides having the amino acid sequences near the Asn residues to which the carbohydrate chains are attached (Asn 413 and Asn 611). The amino acid sequence of transferrin is known (Yang, F., Lum, J. B., McGill, J. R., Moore, C. M., Naylor, S. L., van Bragt, P. H., Baldwin, W. D. and Bowman, B. H., Proc. Natl. Acad. Sci., 81, 2752–2756, 1984), and the sequences near Asn 413 and Asn 611 can be readily determined. Although the sequence of transferrin can vary from individual to individual, the sequences near Asn 413 and Asn 611 are conserved. The size of the peptide may vary, but is preferably about 13 to 14 amino acids in length. Particularly preferred are peptides having the following sequences:

```
Val Leu Ala Glu Asn Tyr Asn Lys Ser Asp Asn Cys Glu
             5                      10
                                       [SEQ ID NO:1]
Gln His Leu Phe Gly Ser Asn Val Thr Asp Cys Ser Gly
             5                      10
                                       [SEQ ID NO:2]
```

The peptides may be synthesized by a solid phase peptide synthesis method like those described in Merrifield, JACS, 85, 2149, 1963; Davis et al., Biochemistry International, 10, 394–414, 1985; Steward and Young, Solid Phase Peptide Synthesis, 1969; U.S. Pat. No. 3,941,763; Finn et al. in The Proteins, 3d ed., volume 2, Neurath et al. ed., pp. 105–253, 1976; and Erickson et al. in The Proteins, 3d ed., volume 2, Neurath et al., ed., pp. 257–527, 1976. The peptides may also be purchased commercially from various sources including the following: Sigma Chemical Co., St. Louis, Mo.; Peninsula Laboratories, Belmont, Calif.; Bachem Inc., Torrance, Calif.; and Vega Biochemicals, Tucson, Ariz.

The peptide may be used to immunize animals directly, but is preferably coupled to an immunogenic carrier before being used. Suitable carriers are compounds capable of stimulating the production of antibodies in a host animal to haptens coupled to them. Such carriers are conventional and well known. They are generally high molecular weight compounds. In most cases, the carrier will be a protein or polypeptide, although other materials such as carbohydrates, polysaccharides, lipopolysaccharides, nucleic acids, and the like of sufficient size and immunogenicity can be used.

Suitable immunogenic carrier proteins and polypeptides will generally have molecular weights between 4,000 and 10,000,000, and preferably greater than 15,000. Suitable carrier proteins and polypeptides include albumins (e.g., bovine serum albumin, ovalbumin, human serum albumin), immunoglobulins, thyroglobulins (e.g., bovine thyroglobulin), hemocyanins (e.g., Keyhole Limpet hemocyanin) and polypeptides such as polylysine or polyalaninelysine.

The peptide is coupled to the carrier using methods well known in the art. For instance, the peptide may be coupled to the carrier with conjugating reagents such as glutaraldehyde, a water soluble carbodiimide, N-N-carbonyldiimidazole, 1-hydroxybenzotriazole monohydrate, N-hydroxysuccinimide, n-trifluoroacetylimidazole cyanogen bromide, 3-(2'-benzothiazolyl-dithio)propionate succinimide ester, hydrazides, or affinity labeling methods. See also Pierce Handbook and General Catalog (1989) for a list of possible coupling agents.

Additional references concerning conventional immunogenic carrier materials and coupling techniques are the following: Erlanger, Meth. Enzymol., 70, 85–104, 1980; Makela and Seppala, Handbook of Experimental Immunology, Blackwell, 1986; Parker, Radioimmunoassay of Biologically Active Compounds, Prentice-Hall, 1976; Butler, J. Immunol. Meth., 7, 1–24, 1974; Weinryb and Shroff, Drug. Metab. Rev., 10, 271–83, 1979; Broughton and Strong, Clin. Chem., 22, 726–32, 1976; Playfair et al., Br. Med. Bull., 30, 24–31, 1974.

The number of peptides coupled to the carrier molecule (the "epitopic density") will range from 1 to the number of available coupling groups on the carrier molecule. The epitopic density on a particular carrier will depend upon the molecular weight of the carrier and the density and availability of coupling sites. Optimal epitopic densities fall between about 10% and about 50% of the available coupling groups on the carrier molecule.

To produce polyclonal antibodies, the immunogen is used to immunize an animal. Methods of immunizing animals are well known and conventional, and suitable immunization protocols and immunogen concentrations can be readily determined by those skilled in the art. For instance, the antibodies of the present invention may be prepared by injecting a suitable host animal (such as a rabbit, goat, horse, or other mammal) with the immunogen of the invention in admixture with an adjuvant (such as Freund's complete or incomplete adjuvants). The injections of immunogen are continued until an antiserum of suitable titer is obtained. The antiserum is harvested and may be further purified using known techniques if needed or desired. For instance, the antibodies may be affinity purified or may be fractionated, such as by DE-52 chromatography.

Alternatively, the antibodies of the invention can be prepared by somatic cell hybridization by fusing cells from an immunized animal (such as rats, hamsters, mice or other mammal) with immortal cells such as myeloma cells. Methods of somatic cell hybridization and for producing monoclonal antibodies are well known.

Briefly, animals are immunized with the immunogen in the same manner as described above for the production of polyclonal antibody. Then, immunized cells capable of producing immunoglobulin (B cells) are harvested from a lymphatic organ of the animal (usually and preferably the spleen). The harvesting of the cells is accomplished by conventional means well known in the art.

As an alternative to the immunization of animals, the stimulation of antigen-specific B cells can be accomplished in vitro. To do so, immunocompetent cells are harvested from lymphatic organs removed from an animal. Procedures for harvesting and in vitro immunization are well known to artisans in the field (Reading, *Meth. Enzymol.*, 121, 18–27, 1986; Gratecos et al., *J. Imm. Meth.*, 103, 169–178, 1985; Mishell and Shiigi, *Selected Methods in Cellular Immunology*, 1980).

Immortal cells suitable for use as fusion partners for the production of hybridomas are well known in the art. Preferably myeloma cells that do not secrete immunoglobulin components are used as the immortal cells.

Fusion is generally performed about 4–5 days after the last injection of immunogen. Fusion can be performed according to any of several well known methods, including polyethylene glycol (PEG) fusion, electrofusion and immunochemical and biochemical methods (see, e.g., Samoilovich et al., *J. Imm. Meth.*, 101, 153–170, 1987).

The fused hybrid cells are selected and cloned by known methods, and hybridomas producing monoclonal antibodies of appropriate specificity are identified by screening the cloned hybrid cells using any of a variety of well known immunoassay techniques. To produce the antibodies of the invention, the selected hybridomas can be cultured in culture medium so that the hybridomas produce and secrete the antibody into the culture medium. Alternatively, the hybridomas can be injected intraperitoneally into animals to cause tumors which produce ascites fluid containing the antibody. Techniques of preparing and purifying monoclonal antibodies are well known (see, e.g., Bodeus et al., *Immunol. Meth.*, 79, 1 (1985); Bazin et al., *Int. J. Cancer*, 10, 568 (1982); Bazin, *Adv. Cancer Res.*, 50, 279 (1987); Bazin, *J. Immunol. Meth.*, 71, 9 (1984)).

A suitable antibody reagent can also be prepared using recombinant DNA techniques. Such techniques are well known and include the production of single-chain antibodies.

Thus, antibody suitable for use in the invention can be monoclonal or polyclonal antibody, can be an antiserum or a purified fraction thereof (such as DE52 fractionated or affinity-purified antibody), can be any of the known isotypes or subclasses (such as IgG, IgM, etc.), can be an antibody fragment (such as Fab, F(ab') or F(ab')$_2$ that is capable of binding antigen, or can be another antibody reagent such as a single-chain antibody reagent. The only requirement for the antibody is that it have specificity for at least one alcoholic transferrin homolog.

The antibodies of the invention can be used in any immunoassay method that allows the detection or quantitation of an alcoholic transferrin homolog in a body fluid. Many such immunoassay techniques are known. Suitable immunoassay methods include radioimmunoassay, enzyme immunoassay and fluorescence immunoassay. The immunoassay may be done in the competitive binding format or may be an immunometric assay. It may be a homogenous or heterogenous assay. Suitable homogenous techniques are fluorescence quenching and enhancement, energy transfer immunoassay, double antibody steric hindrance immunoassay, substrate-labeled immunoassay, prosthetic group-labeled immunoassay and enzyme modulator-labeled immunoassay. The immunoassay may be automated or performed manually.

To perform the immunoassay, a sample of a body fluid containing transferrin is brought into contact with an antibody according to the invention which reacts selectively with an alcoholic transferrin homolog. The body fluid may be serum, plasma, saliva, or other body fluid, but is preferably serum.

One of the reagents used in the immunoassay must be labeled to allow for detection or quantitation of the alcoholic transferrin homolog. Suitable labels are well known in the art. They include the following: 1) enzymes (e.g., horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase and acetylcholine esterase); 2) fluorophores (such as fluorescein isothiocyanate, rhodamine, phycoerythrin, phycocyanin, allophycocyanin, o-phthaldehyde and fluorescamine); 3) radionucleotides (such as $^{125}$I); 4) bioluminescent labels (such as luciferin, luciferase and aequorin); 5) chemiluminescent labels (such as luminol, isoluminol, aromatic acridinium ester, imidazole, acridinium salt and oxalate ester); and 6) biotin. The binding of these labels to the desired reagent and the detection of the labels can be accomplished using standard techniques well known to those skilled in the art.

A preferred immunoassay construct is a sandwich (capture, two-site) assay. In this assay, antibody which reacts selectively with an alcoholic transferrin homolog is immobilized on a solid surface. Then the body fluid is brought into contact with the solid surface, and the alcoholic transferrin homolog in the body fluid binds to the immobilized antibody. After washing away unbound material, a labeled component is added which binds to the alcoholic transferrin homolog already bound to the immobilized antibody. Suitable labels are those listed above. This labeled component is preferably a labeled antibody reactive with all transferrin homologs. The amount of the bound labeled component is proportional to the amount of the alcoholic transferrin homolog in the original sample. Alternatively, the antibody bound to the solid surface could be the antibody reactive with all transferrin homologs, and the labeled antibody could be the antibody which reacts selectively with an alcoholic transferrin homolog.

Suitable solid surfaces for use in the above assay and in other assay constructs requiring a solid surface are well known. They include polystyrene, glass, polypropylene, polyethylene, nylon, polyacrylamide, agarose, latex, and paper. The solid surface may be the wells of a microtiter plate, the inside surface of a vial or test tube, a dip strip or latex beads.

Another preferred assay is a competitive assay. In this assay, a limited amount of an antibody which reacts selectively with an alcoholic transferrin homolog is immobilized on a solid surface. Suitable solid surfaces are those listed above. To perform the assay, the body fluid and a labeled component are added simultaneously to the immobilized antibody. The labeled component will compete with the alcoholic transferrin homologs in the body fluid for binding to the limited amount of the antibody. The labeled component can be labeled immunogen, such as the peptides and peptide-carriers whose preparation is described above. Suitable labels are those listed above. The amount of the labeled component bound to the immobilized antibody will be inversely proportional to the amount of the alcoholic transferrin homolog present in the body fluid.

The specific concentrations, the temperature and time of incubation, as well as other assay conditions, can be varied in whatever immunoassay is employed depending on such factors as the concentration of the alcoholic transferrin homolog in the sample, the nature of the sample, and the like. Those skilled in the art will be able to determine operative and optimal assay conditions by routine experimentation.

The invention also comprises a kit for detecting or quantitating an alcoholic transferrin homolog. The kit is a packaged combination of one or more containers holding reagents useful in performing the immunoassays of the invention. Suitable containers for the reagents of the kit include bottles, vials, test tubes and microtiter plates.

The kit will comprise a container of an antibody which reacts selectively with an alcoholic transferrin homolog. The antibodies are those described above, and they may be labeled with the labels listed above if they are to be used to detect or quantitate the alcoholic transferrin homolog. The antibodies may be in solution, may be lyophilized or may be bound to a solid surface, such as those solid surfaces described above.

If the antibody which reacts selectively with an alcoholic transferrin homolog is not labeled, the kit may also comprise a container of a labeled component useful for detecting or quantitating the amount of the alcoholic transferrin isoform present in the body fluid. This labeled component may be a labeled antibody which is reactive with all transferrin homologs or a labeled immunogen, or may be a labeled peptide coupled to poly-L-lysine for fluorescence polarization.

Finally, the kit may contain other materials which are known in the art and which may be desirable from a commercial and user standpoint such as buffers, enzyme substrates, diluents, standards, etc. The kit may also include containers such as test tubes and microtiter plates for performing the immunoassay.

It is believed that glycoproteins other than transferrin may have altered patterns of glycosylation in alcoholics. Thus, it is believed that the principles of the present invention can be extended to produce antibodies that react selectively with homologs of these other glycoproteins found in alcoholics but not in non-alcoholics and that these antibodies can be used to detect and quantitate the alcoholic homologs of these other glycoproteins.

Further, it is believed that the principles of the present invention can be extended to detect and quantitate the transferrin and other glycoprotein homologs found in the genetic syndrome discussed in the Background section which is characterized by carbohydrate deficient serum glycoproteins. Indeed, it is believed likely that the antibodies described herein which react selectively with alcoholic transferrin homologs may react selectively with transferrin homologs found in those suffering from this syndrome.

EXAMPLES

Example 1

Preparation Of Immunogens

As discussed in the Background section, it has generally been thought that the pI 5.7 and 5.9 isoforms of transferrin were partially desialylated. These are the transferrin isoforms that are increased in alcoholism. It had also been suggested that the pI 5.7 and 5.9 isoforms may lack some galactose and N-acetyl-glucosamine moieties as well. Stibler, H. and Borg., J. *Alcohol Clin. Exp. Res.*, 10, 61–64, 1986. However, prior to the present invention, no one had contemplated the possibility that a complete biantennary carbohydrate chain might be missing.

If a portion of the pI 5.7 and 5.9 isoforms were galactose-terminated as generally believed prior to the present invention (i.e., desialyated), then an assay to detect galactose could be devised. An effort was made to develop such an assay using anti-human transferrin to capture transferrin from serum and using biotin-labeled *Ricinus communis* I (RCA-I) lectin to quantitate galactose-terminal moieties. Several permutations of this assay were tried, but RCA-I reactivity with alcoholic sera containing 6–15% of the pI 5.7 isoform could not be demonstrated. The assay system, however, did accurately quantitate the partially desialylated transferrin standards which were prepared by treating transferrin with neuraminidase.

Accordingly, an experiment was performed to more directly determine the chemical difference between the alcoholic pI 5.7 isoform and the normal pI 5.4 isoform. The pI 5.7 isoform was isolated from the serum of an alcoholic by multiple runs on a Mono-P chromatofocusing gel column (Pharmacia, Uppsala, Sweden) as described in Storey et al., *Clin. Chem.*, 3119, 1543, 1985. The pI 5.7 fractions were pooled and shown to be at least 90% pI 5.7 isoform by isoelectric focusing. Differential acid hydrolysis was performed on the purified fraction as described in Hardy, M. R., Townsend, R. R. and Lee, Y. C., *Anal. Biochem.*, 170, 54–62, 1988. Carbohydrate compositional analysis was next performed on a Dionex LC (HPLC) system (Dionex Corp., Sunnvale, Calif.). The results showed a ratio of galactose:N-acetylglucosamine:mannose of about 2:4:3 for the pI 5.7 isoform, and the same ratio was obtained for the pI 5.4 isoform. However, the total percentages of each carbohydrate per unit weight of the pI 5.7 isoform were almost one-half those obtained with the pI 5.4 isoform. Based on these data we postulated that most of the pI 5.7 isoform in alcoholics lacks one of the two bi-antennary oligosaccharide chains.

It was reasoned that, in the absence of one of these chains, the amino acids surrounding the Asn residues to which the chains are attached (Asn 413 or 611) would be exposed. Accordingly, immunogens were designed which could be used to elicit antibodies to the regions near Asn 413 and 611 which would be exposed if one of the biantennary chains was missing.

A. Peptide Synthesis

Two peptides corresponding to amino acids 405–417 and 607–619 of the amino acid sequence of human transferrin (Yang, F., Lum, J. B., McGill, J. R., Moore, C. M., Naylor, S. L., van Bragt, P. H., Baldwin, W. D. and Bowman, B. H., *Proc. Natl. Acad. Sci.*, 81, 2752–2756, 1984) were synthesized. These peptide sequences were chosen because the Asn residues at positions 413 and 611 are normally glycosylated, and the amino acids near these residues would be exposed if the carbohydrate chains attached to these Asn residues were not present or were substantially truncated. The sequences of the two peptides that were synthesized are presented below:

Val Leu Ala Glu Asn Tyr Asn Lys Ser Asp Asn Cys Glu
 5 10
 [SEQ ID NO:1]

This peptide is designated herein as P1.

Gln His Leu Phe Gly Ser Asn Val Thr Asp Cys Ser Gly
 5 10
 [SEQ ID NO:2]

This peptide is designated herein as P2.

P1 and P2 peptides were synthesized on an Applied Biosystem, Model 431A peptide synthesizer using tertiary butyl oxycarbonyl (BOC) amino acid chemistry. The protective groups were removed with liquid hydrogen fluoride.

B. Peptide Conjugation

The peptides were coupled to bovine serum albumin (BSA) (Sigma Chemical Co., St. Louis, Mo.) or Keyhole Limpet hemocyanin (KLH) (Sigma Chemical Co., St. Louis, Mo.) using carbodiimide as follows. A solution of 2 mg of peptide P1 or P2 in 0.5 ml of distilled water was mixed with 2 mg of BSA or KLH in 0.2 ml of distilled water. Ten mg of carbodiimide was added, and the reaction was allowed to proceed for 2 hours at room temperature. The reaction mixture was then dialyzed exhaustively against distilled water at 4° C. Controls in which distilled water was substituted for peptide were included for assessment of both the extent of conjugation and the specificity of the antibody. UV spectra (280 mm) were obtained for the conjugates, carrier protein and peptides, and the extent of conjugation calculated from the ratio of optical density (ODs) at 230 and 280 nm to yield the moles of peptide per mole of carrier protein. The conjugates that were prepared, carbodiimide used as coupling agent and moles of peptide per mole of carrier protein are shown in Table 1.

TABLE 1

| Conjugates | Coupling Agent | Moles of Peptide/ Mole of Carrier Protein |
| --- | --- | --- |
| P1-BSA | EDC[1] | 12 |
| P2-BSA | EDC | not determined[3] |
| P1-BSA | CMC[2] | 23 |
| P2-BSA | CMC | 25 |
| P1, P2-KLH | EDC | not determined[3] |

[1]EDC = 1-ethyl-3-(dimethylaminopropyl) carbodiimide (HCl) (Pierce Chemical Co., Rockford, IL)
[2]CMC = 1-cyclohexyl-3-(2-morpholinoethyl) carbodiimide (metho-p-toluenesulfonate salt) (Pierce Chemical Co., Rockford, IL)
[3]The P2-BSA and P1- and P2-KLH ratios were not determined as the greater portion of the conjugates were insoluble.

Example 2

Preparation of Rabbit Polyclonal Antibody To Alcoholic Transferrin Homologs

A. Immunization Of Rabbits

A New Zealand White female rabbit (Langshaw Farm, Augusta, Ga., U.S.A.) was initially immunized by the method of Vaitakaitis et al. (*Clin. Endo. Metab.*, 33, 988, 1971) with 2 ml of an emulsion consisting of Freund's complete adjuvant (CFA) (ICN Immunobio-logicals, Lisle, Ill., U.S.A.) containing 300 μg each of peptide P1 conjugated to BSA (P1-BSA) and peptide P2 conjugated to BSA (P2-BSA) prepared as described in Example 1. Two subsequent immunizations were performed using 2 ml of an emulsion of Freund's incomplete adjuvant (IFA) (ICN Immunobiologicals, Lisle, Ill., U.S.A.) containing 300 μg each of P1-BSA and P2-BSA. These subsequent immunizations were done 3 and 5 weeks after the initial immunization. The rabbit was bled (30 ml) from the ear seven days after the third injection by the method of Nerenbert et al. (*J. Immunol. Meth.*, 24, 19, 1978). The serum was tested as described below in section F and then stored frozen at −20° C. prior to further use.

B. Preparation Of Anti-Human Transferrin-Sepharose

To affinity purify transferrin from human sera (normal and alcoholic), an immunosorbent was prepared by adding 40 mg of anti-human transferrin (AXELL, Accurate Chemical & Scientific Corporation, Westbury, N.Y., U.S.A.) to 2g of CNBr-activated SEPHAROSE® (cross-linked agarose 4B (Pharmacia Fine Chemicals AB, Uppsala, Sweden) (prewashed according to the manufacturer's instructions) in 0.1M NaHCO$_3$ (pH 8.3) containing 0.5M NaCl. The mixture was then mixed by inversion overnight at 4° C. The immunosorbent was next transferred to 0.2M glycine buffer (pH 8.0) and mixed by inversion for 2 hours at room temperature. The gel was then washed alternately with: a) 0.1M sodium bicarbonate (pH 8.0) containing 0.5M sodium chloride; and b) 0.1M sodium acetate (pH 4.0) containing 0.5M sodium chloride. Next, the gel was suspended in PBS (0.01M sodium phosphate buffer, pH 7.3, containing 0.15M NaCl) and was stored in the presence of 0.02% NaN$_3$ prior to use.

C. Purification Of Human Transferrin

Affinity purification of human transferrin was accomplished by placing 3 ml of the anti-transferrin-Sepharose 4B prepared as described above in a Bio-Rad disposable polypropylene econo-column (Bio-Rad Laboratories, Richmond, Calif., U.S.A.). The matrix was then washed with 10 ml of PBS. The washed matrix was incubated with rotation for 2 hours at room temperature with 1 ml of human serum (normal or alcoholic). Unbound material was collected and the matrix was washed two times with 10 ml PBS followed by 2 ml of 2M potassium iodide and then 10 ml PBS. The bound transferrin was eluted with 2 ml of 0.1M glycine, to which hydrochloric acid had been added to adjust the pH to 2.3. The eluted transferrin was immediately neutralized, dialyzed against 2 liters of water overnight at 4° C., and finally lyophilized.

D. Neuraminidase Treatment Of Affinity-Purified Transferrin

Transferrin which had been affinity purified as described above was digested by neuraminidase (Sigma Chemicals, St. Louis, Mo., U.S.A.) according to the manufacturer's instructions. Briefly, 20 μg transferrin in a total of 30 μl aqueous solution with 2 mM sodium acetate (pH 5.0) was incubated with 30 milliunits of neuraminidase for one hour at 37° C. Then the preparation was used in screening assays (see below).

E. N-glycanase Treatment Of Affinity-Purified Transferrin

Transferrin was digested with N-glycanase by the method of Hirani, et al., *Anal. Biochem.*, 162, 485–92, 1987. Transferrin at a concentration of 0.5 μg/μl in a total volume of 25 μl of 150 mM sodium phosphate (pH 7.6) was incubated with 1 unit of N-glycanase at 37° C. for 18 hours. Then the preparation was used in screening assays (see below).

F. Screening Of Rabbit Antiserum

The rabbit antiserum was tested against the following antigens using the method described in Example 3, part B: 1) all of the peptide conjugates listed in Table 1; 2) carbodiimide-treated BSA and KLH; 3) BSA and KLH (untreated); 4) P1 and P2; 5) affinity-purified normal and alcoholic transferrins; 6) neuraminidase-treated affinity-purified normal and alcoholic transferrins; and 7) N-glycanase-treated affinity-purified normal and alcoholic transferrins. The antiserum showed high reactivities to the peptide-conjugates, carrier proteins and P1 and P2. It also exhibited reactivity to the N-glycanase-treated transferrin, and it exhibited greater reactivity with affinity-purified alcoholic transferrin than with affinity-purified normal transferrin. Accordingly, the IgG fraction of the rabbit antiserum was obtained for further testing.

Example 3

Reactivity Of The IgG Fraction Of The Rabbit Antiserum To Alcoholic And Normal Transferrins

A. Purification And Labeling Of IgG Fraction

A "Gamma Bind Pre Pack" protein G column (Genex Corporation, Gaithersburg, Md., U.S.A.) was used to purify the IgG fraction of the rabbit anti-P1 and P2 serum prepared as described in the previous Example. One ml of the rabbit antiserum was diluted 1:1 with 0.01M phosphate buffer (pH 6.0) containing 0.15M NaCl (binding buffer) and loaded onto the protein G column (1 ml/minute). Next the column was washed with 10 ml of the binding buffer. Elution was accomplished using 4 ml of 0.1M glycine HCl (pH 3.0). Eluted fractions containing the IgG were collected, directly neutralized with 0.1M sodium phosphate buffer, pH 9.2, containing 0.15M NaCl and then dialyzed against PBS (0.01M sodium phosphate buffer, pH 7.3, containing 0.15M NaCl ). A portion of the purified IgG fraction of the rabbit antibody was subsequently labeled with biotin according to the method of Kendall et al. (*J. Immunol. Meth.*, 56:329, 1983).

B. Assay Of The IgG Fraction Of The Rabbit Antibody

The wells of a polystyrene microtiter plate (Immunolon 2, Cooke Engineering Co., Alexandria, Va., U.S.A.) were coated by adding 100 µl of a 5 µg/ml solution of the IgG fraction of the rabbit antibody specific for human transferrin peptides P1 and P2 (preparation described in the previous section) in 0.1M sodium bicarbonate (pH 9.0) to each well and incubating the plate for two hours at 37° C. Unbound antibody was removed by decanting, and the remaining polystyrene protein-binding sites were blocked by filling the wells with a 1% solution of ovalbumin in PBS and incubating the plate for one hour at 37° C. The wells were then washed three times with PBS.

Next, 100 µl/well of a solution of 20 µg/ml of affinity-purified transferrin (normal or alcoholic) (prepared as described Example 2) in PBS were added to each well and left to incubate overnight at 4° C. The wells were then washed three times with PBS and 100 µl of sheep antibody to human transferrin labeled with horseradish peroxidase (Biodesign International, Kennebunkport, Me., U.S.A.) at a 1:6500 dilution in PBS were added, and the plate was incubated for two hours at 37° C. The color reaction was developed with 0.8 mg/ml of the substrate o-phenylenediamine-2 HCl (OPD) in substrate buffer (0.1M $Na_2HPO_4$, 0.05M citrate monohydrate, pH 5.0, 0.015% hydrogen peroxide) for 20 minutes at room temperature. The reaction was then stopped by the addition of 50 µl of 2N sulfuric acid, and the absorbance at 492 nm read with a Titertek Multiskan (Flow Laboratories, McClean, Va., U.S.A.).

Control wells were prepared in an identical manner as described above, except some had no adsorbed antibody (without adsorbed antibody control), some had no transferrin (without antigen control), and some had neither adsorbed antibody nor antigen (substrate control). These controls were used to correct the readings for non-specific binding of antigen and labeled antibody and for non-enzymatic substrate hydrolysis. The results of this assay are presented in Table 2.

TABLE 2

| Transferrin Source | Alcoholic/ Normal | OD (492 nm) |
|---|---|---|
| Ho | Alcoholic | 0.227 |
| Ni | Alcoholic | 0.548 |
| Ro | Alcoholic | 0.499 |
| BL | Alcoholic | 0.134 |
| AT-1 | Alcoholic | 0.277 |
| AT-2 | Alcoholic | 0.160 |
| 49 | Alcoholic | 0.077 |
| 38 | Alcoholic | 0.099 |
| 47 | Alcoholic | 0.161 |
| 16 | Alcoholic | 0.143 |
| 8 | Alcoholic | 0.126 |
| 17 | Alcoholic | 0.221 |
| 45 | Alcoholic | 0.134 |
| 48 | Alcoholic | 0.139 |
| Si | Normal | 0.084 |
| MV | Normal | 0.063 |
| BA | Normal | 0.056 |
| SM | Normal | 0.001 |

Statistical analysis of the data (alcoholic versus normal transferrins) by a two-sample t-test, with variances either assumed to be equal or unequal, yielded a p value of <0.001 for the reactivity of the IgG fraction of the rabbit antibody to transferrin peptides P1 and P2 with alcoholic versus normal transferrin. The means and standard deviations were 0.051±0.0035 for normal transferrin and 0.210±0.143 for alcoholic transferrin. Only two of the fourteen values for alcoholic transferrin fell within the mean of the values for normal transferrin plus two standard deviations. Accordingly, it was concluded that the rabbit antibody to transferrin peptides P1 and P2 showed significantly greater reactivity to alcoholic transferrins than to normal transferrins.

Example 4

Binding Of Biotin-Labeled IgG Fraction Of The Anti-Transferrin Peptides P1 and P2 Antibody To Affinity-Purified Transferrins Affinity-purified transferrins (400 ng) from alcoholic and normal sera (prepared as described in Example 2) were adsorbed to the wells of Microfluor "B" black polystyrene microtiter plates (Dynatech Laboratories, Alexandria, Va., U.S.A.) at a concentration of 5 µg/ml protein in 0.1M sodium bicarbonate (pH 9.0) for two hours at 37° C. Unbound antigen was removed by decanting. The remaining polystyrene protein-binding sites were blocked by filling the wells with a 1:45 dilution of fish skin gelatin (Sigma Chemical Company, St. Louis, Mo., U.S.A.) in PBS, and incubating the plates for one hour at 37° C. The microtiter wells were then washed three times with PBS, and 100 µl of the IgG fraction of rabbit anti-transferrin peptides P1 and P2 antibody labeled with biotin (prepared as described in Example 3) at a dilution of 1:100 were added to the wells and incubated for two hours at 37° C. After three washes with PBS, 100 µl of streptavidin-β-galactosidase (Bethesda Research Laboratories, Gaithersburg, Md., U.S.A.) diluted at 1:2000 in PBS containing 1% BSA were added to the plates, and the plates were incubated for one hour at 37° C. After three washes with PBS, 100 µl of 0.1 µg/ml solution of 4-methyl-umbelliferyl-β-D-galactopyranoside in 0.01M sodium phosphate buffer (pH 7.5) containing 0.1M sodium chloride and 1 mM magnesium dichloride were added to the wells of the microtiter plate. The methyl-umbelliferone fluorescence was measured as relative fluorescence units (RFU) using an excitation wavelength of 365 nm and an emission wavelength of 450 nm.

Control wells were prepared in an identical manner as described above except that some had no adsorbed antigen (without antigen control); some had no primary antibody (rabbit-anti-transferrin IgG) (without primary antibody control); some had no antigen or primary antibody (streptavidin-β-galactosidase control); some had no antigen, no primary antibody and no streptavidin-β-galactosidase (substrate control). The without-antigen control and the without-primary-antibody or streptavidin-β-galactosidase control served to correct readings for non-specific binding of antibody and labelling reagents, while the substrate control corrected for non-enzymatic substrate hydrolysis.

The results are presented in Table 3.

TABLE 3

| Source Of Transferrin | Type | Relative Fluorescent Units |
| --- | --- | --- |
| GG-1 | alcoholic | 143 |
| OL | alcoholic | 307 |
| TT | alcoholic | 563 |
| MD | alcoholic | 263 |
| GG-2 | alcoholic | 708 |
| CD | alcoholic | 1,078 |
| AM | alcoholic | 756 |
| GR | alcoholic | 908 |
| AT-1 | alcoholic | 941 |
| AT-2 | alcoholic | 732 |
| BL | alcoholic | 125 |
| SC | normal | 87 |
| BA | normal | 216 |
| SM | normal | 31 |
| MV | normal | 0 |

The mean and standard deviation for the alcoholic transferrins were 593±320 and for the normal transferrins were 84±83. The t-test of estimation of the significance of the differences of the two means yielded a p value of <0.001. Two of the eleven alcoholic values fell below the sum of the normal mean plus two standard deviations; one of the normals was relatively high but did not exceed the sum of the normal mean plus two standard deviations. It was concluded that the rabbit antiserum produced to the transferrin peptides P1 and P2 had an antibody population with specificity for transferrin preparations from alcoholic sera.

Example 5

Preparation Of Monoclonal Antibody To Alcoholic Transferrin Homologs

A. Immunization Of Mice

Balb/c mice (Sprague-Dawley Inc., Indianapolis, Ind., U.S.A.) were immunized using the method of Vaitakaitis et al., Clin. Endo. Metab., 33, 988, 1971. Initially, each 6-week-old mouse was injected intraperitoneally with 0.1 ml of an emulsion consisting of CFA containing 20 μg each of P1-KLH and P2-KLH (prepared as described in Example 1). Subsequently, the mice were immunized with 0.1 ml of an emulsion of IFA containing 15 μg each of P1-KLH and P2-KLH. Five subsequent immunizations were performed at 30-day intervals after the initial injection for a total of six injections.

The mice were bled after the third and sixth injections, and the sera tested against several antigens as described in Example 2, section F, for the rabbit antiserum. As expected, all of the antisera showed high reactivities to the peptide-conjugates and carrier proteins. Two mice showed high reactivity to P2 but not to P1. One mouse showed reactivity to the N-glycanase-treated transferrin, and all of the antisera revealed a difference in their reactivities with alcoholic versus normal transferrin.

Hybridomas were produced from the one mouse reactive with N-glycanase-treated transferrin. Four days before fusion, the mice were injected intravenously with 20 μg of affinity purified alcoholic transferrin and 60 μg of purified alcoholic pI 5.7 isoform (prepared as described in Example 1).

B. Production Of Hybridomas

A single cell suspension of spleen cells from the immunized Balb/c mouse was prepared by crushing the spleen between two sterile glass slides and resuspending the cells in culture media (HL1 Media, available from Endotronics, Coon Rapids, Minn., U.S.A.), supplemented with 1% FCS, penicillin (100 units/ml), streptomycin (100 micrograms/ml) and glutamine (0.03%) (all from Gibco, Grand Island, N.Y., U.S.A.). Then $5 \times 10^7$ spleen cells were incubated with $2.5 \times 10^7$ HLI-653 mouse myeloma cells (ATCC, Bethesda, Md., U.S.A.) with 1 ml polyethylene glycol according to the method of Kohler, G. and Milstein, C. Nature, 256, 495, 1975, pelleted and fused. Hybrid cells were selected by growth on HAT (hypoxanthine, aminopterin and thymidine) and AAT (adenosine, aminopterin and thymidine) media. Hybridoma cultures were cloned by limiting dilution until stable lines were obtained. Hybridoma culture supernatants were screened as described below in section C.

C. Screening Of Hybridomas

Monoclonal antibodies produced by the hybridomas were screened against P2 and affinity-purified transferrins from alcoholic and normal sera using using the method of Example 4, except that alkaline phosphatase labeled goat anti-mouse IgG+IgM antibody was used to detect the bound monoclonal antibody, rather than using biotin-labeled monoclonal antibody.

Briefly, the wells of polystyrene microtiter plates were coated overnight with 800 ng/well of peptide P2 or 400 ng/well of affinity-purified transferrin from alcoholic or normal serum in 0.05M carbonate buffer (pH 9.6). After washing, the wells were backcoated by incubating with a 1% BSA-PBS solution at room temperature for 30 minutes. Next, 100 μl of the culture supernatants of the hybridoma clones were added to the wells, and the plates were incubated for 16 hours at 4° C. After washing three times with PBS containing 0.5% Tween 20 (Sigma Chemical Co., St. Louis, Mo.), 100 μl of a 1:1000 dilution of alkaline phosphatase labeled anti-mouse IgG+IgM reagent (catalog No. A108AN from American Qualex, LaMarinda, Calif., U.S.A.) were added to the wells, and the plates were incubated 60 minutes at room temperature. After washing three times with PBS, 100 microliters of a 1 μg/ml phosphatase substrate solution (Sigma 104, from Sigma, St. Louis, Mo., U.S.A.) in substrate buffer consisting of 5.3 g/l $Na_2CO_3$ mM, 0.4 g/l $MgCl_2 \cdot 6H_2O$ and 2 g/l $NaN_3$ (pH 9.5) were added to the plates. Next the plates were incubated for 60 minutes at room temperature. Then the OD at 405 nm was read using a kinetic microplate reader (Molecular Devices, Menlo Park, Calif., U.S.A.). The results are presented in Table 4.

TABLE 4

| Group | Number of Clones | Peptide P2[2] | OD 405[1] screening against: Alcoholic Transferrin[3] | Normal Transferrin |
|---|---|---|---|---|
| 1 | 2 | 0.136–1.116 | 0.312–0.404 | 0.033–0.070 |
| 2 | 9 | 0.297–2.377 | 0.319–0.940 | 0.266–0.785 |
| 3 | 3 | 0.054–0.135 | 0.050–0.072 | 0.253–0.278 |
| 4 | 3 | 0.274–0.356 | 0.057–0.086 | 0.024–0.095 |

[1]OD 405 = OD at 405 nm, readings of p-nitrophenol product formed in 30 minutes.
[2]The mouse (serum) used to produce these hybridomas only reacted with peptide 2 and not to peptide 1 when the peptides alone were adsorbed to the polystyrene wells as antigen targets.
[3]The transferrins were affinity purified using an anti-transferrin affinity column as described in Example 2.

Group 1 contains clones producing antibodies reactive with peptide P2 and alcoholic transferrin, but not with normal transferrin. The 4C9 clone is one of the two clones in this group. Isotyping using a mouse isotyping kit available from Boehringer Mannheim showed that the 4C9 clone produces IgM antibody.

Group 2 contains clones reacting with all 3 antigen targets (peptide P2 and alcoholic and normal transferrin).

Group 3 contains clones reacting apparently with only normal transferrin.

Group 4 contains clones reacting only with peptide P2.

Example 6

Reactivity Of 4C9 Monoclonal Antibody With Alcoholic, Normal, Neuraminidase-Treated And N-Glycanase-Treated Transferrins The reactivity of 4C9 monoclonal antibody against affinity-purified alcoholic and normal transferrins, neuraminidase-treated transferrin and N-glycanase-treated transferrin was tested as describe in Example 5. To do so, the wells of microtiter plates were coated with 400 nanograms of each antigen, and the rest of the assay was performed as described in Example 5. The results are presented in Table 5.

TABLE 5

| Transferrin[1], Source, Treatment | OD (405 nm)[2] |
|---|---|
| JM[3], abstinent alcoholic | 0.009 |
| JM, abstinent alcoholic, neuraminidase | −0.013[4] |
| JM, abstinent alcoholic, N-glycanase | 0.561 |
| AT-1, alcoholic | 0.124 |
| RF, alcoholic | 0.034 |
| JM-2, alcoholic | 0.023 |
| NG, alcoholic | 0.115 |
| AT-2, alcoholic | 0.026 |
| HH, alcoholic | 0.029 |
| JW, alcoholic | 0.035 |
| PB, normal | −0.004 |
| Peptide P2 | 0.576 |

[1]The transferrins were affinity isolated as described in Example 2.
[2]The optical densities at 405 nm are the readings of the product formation (p-nitrophenol) via the action of the alkaline phosphatase enzyme; non-specific adsorption of monoclonal antibody has been subtracted.
[3]Initials (codes) for individual derived transferrins.
[4]A negative OD reading indicates that the control for non-specific monoclonal antibody binding was greater than the experimental value.

As Table 5 shows, 4C9 monoclonal antibody reacts with deglycosylated (N-glycanase treated) transferrin and with affinity-purified transferrins from known alcoholic sera. It does not react significantly with transferrins from normal or abstinent sera. Note that JM was an alcoholic patient who had abstained for three weeks before the serum specimen was obtained. Also, 4C9 antibody does not react with desialylated (neuraminidase treated) transferrin.

Preliminary experiments have been conducted to determine whether 4C9 reacts with the pI isoforms shown by the prior art to be associated with alcoholism. To do so, isoelectric focusing was performed on the transferrin preparations listed in Table 5 using a pH gradient of 4–8. Two bands (pI 5.7–5.8 and 6.1–6.2) were found to be characteristic of alcoholic transferrin preparations, although one of the bands (pI 5.7–5.8) was found in the untreated normal transferrin preparation. The results of the isoelectric focusing were compared with the results of the above immunoassay and showed an approximate relationship between the activity of 4C9 in the immunoassay and the intensity of the pI 5.7–5.8 and 6.1–6.2 bands. The fact that the correlation was only approximate indicates that the pI 5.7–5.8 and 6.1–6.2 bands probably contain non-alcoholic transferrin homologs and that alcoholic transferrin homologs are probably found in other pI bands.

Example 7

Reactivity Of 4C9 Monoclonal To Transferrin Preparations From Alcoholic And Normal Patients Example 6 was repeated using one microgram (rather than 400 nanograms) samples of affinity purified alcoholic and normal transferrins adsorbed to the microtiter plate wells. Also, the transferrin preparations were reacted with monoclonal antibody 1C11 which reacts with all transferrins (alcoholic and normal), as well as with monoclonal antibody 4C9. the optical densities were corrected for non-specific binding. The results are presented in Table 6.

TABLE 6

| Transferrin Preparation | OD 405 nm 4C9 (anti-alcoholic transferrin) | OD 405 nm 1C11 (anti-transferrin) |
|---|---|---|
| AT-1, alcoholic | 0.431 | 0.169 |
| MD, alcoholic | 0.092 | 0.177 |
| CD, alcoholic | 0.159 | 0.161 |
| OL, alcoholic | 0.070 | 0.171 |
| HH, alcoholic | 0.108 | 0.157 |
| GA, normal | 0.004 | 0.110 |
| MI, normal | 0.015 | 0.119 |
| JE, normal | 0.009 | 0.157 |
| JA, normal | 0.004 | 0.159 |
| SI, normal | 0.002 | 0.143 |

Little reactivity of 4C9 antibody with normal transferrins was detected; the reactivity of 4C9 with alcoholic transferrins was clearly and significantly higher than with transferrins affinity purified from normal sera. The 1C11 antibody reacted essentially the same with alcoholic and normal transferrins, showing that approximately the same amounts of transferrins (normal or alcoholic) were adsorbed to the polystyrene microtiter plate wells. The means and standard deviations of the 4C9 antibody reactivities with normal and alcoholic transferrins were 0.0068±0.0047 and 0.172±0.132, respectively; statistical comparisons of the means for the significance of these differences yielded a p value of <0.05. None of the five alcoholic transferrin values were less than the sum of the normal mean plus two standard deviations.

Preliminary experiments have been conducted to determine whether 4C9 reacts with the pI isoforms shown by the prior art to be associated with alcoholism. To do so, isoelectric focusing was performed on the alcoholic and normal transferrin preparations listed in Table 6 using a pH gradient of 4–8. As in the previous example, the results of the immunoassay showed an approximate relationship to the intensity of the pI 5.7–5.8 and 6.1–6.2 bands. The fact that the correlation was only approximate indicates that the pI 5.7–5.8 and 6.1–6.2 bands probably contain non-alcoholic transferrin homologs and that alcoholic transferrin homologs are probably found in other pI bands.

said non-alcoholics and is not accessible to the antibody in said non-alcoholics.

2. An antibody which reacts selectively with a transferrin homolog lacking an amount of oligosaccharide chain normally attached to transferrin at positions Asn 413 and/or Asn 611, said amount sufficient to expose an epitope on the transferrin homolog within about 14 amino acid residues of Asn 413 and/or Asn 611 that is not exposed in said non-alcoholics and is selectively bound by the antibody in said alcoholics but is not by the antibody in said non-alcoholics.

3. The antibody according to claim 2 which is a monoclonal antibody.

4. The monoclonal antibody according to claim 3 which is produced by a hybridoma prepared by fusing mouse myeloma cells with spleen cells from a mouse immunized with one or both of the following two peptides, each peptide conjugated to an immunogenic carrier:

---

---

We claim:

1. An antibody which reacts selectively with a transferrin homolog found in alcoholics, wherein said alcoholics are individuals who ingest 60 grams or more of ethanol per day for a period of one week or more, but not found in non-alcoholics, wherein said non-alcoholics are individuals who do not ingest 60 grams or more of ethanol per day for a period of one week or more, and wherein said homolog lacks an amount of carbohydrate chain normally attached to Asn 413 and/or Asn 611 in a transferrin molecule, said amount sufficient to expose an epitope within about 14 amino acid residues of Asn 413 and/or Asn 611 that is not exposed in Val Leu Ala Glu Asn Tyr Asn Lys Ser Asp Asn Cys Glu
                5                    10
[SEQ ID NO: 1]
and
Gln His Leu Phe Gly Ser Asn Val Thr Asp Cys Ser Gly
                5                    10
[SEQ ID NO: 2].

5. The monoclonal antibody according to claim 4 which is an IgM class monoclonol antibody.

6. The antibody according to claim 2 which is a polyclonal antibody.

7. The polyclonal antibody according to claim 6 which is produced by a rabbit immunized with one or both of the following two peptides, each peptide conjugated to an immunogenic carrier:

Val Leu Ala Glu Asn Tyr Asn Lys Ser Asp Asn Cys Glu
                5                        10
[SEQ ID NO: 1]
and
Gln His Leu Phe Gly Ser Asn Val Thr Asp Cys Ser Gly
                5                        10
[SEQ ID NO: 2].

8. An antibody which reacts selectively with a transferrin homolog, the antibody being produced by immunizing an animal with one or both of the following two peptides, each peptide conjugated to an immunogenic carrier:

Val Leu Ala Glu Asn Tyr Asn Lys Ser Asp Asn Cys Glu
                5                        10
[SEQ ID NO: 1]
and
Gln His Leu Phe Gly Ser Asn Val Thr Asp Cys Ser Gly
                5                        10
[SEQ ID NO: 2];

or antibody that reacts selectively with a transferrin homolog in alcoholics, wherein said transferrin homolog lacks an amount of carbohydrate chain normally attached to Asn 413 and/or Asn 611 in a transferrin molecule, said amount sufficient to expose an epitope within about 14 amino acid residues of Asn 413 and/or Asn 611 that is not exposed in non-alcoholics and is selectively bound by either said antibody.

9. A hybridoma which produces a monoclonal antibody which reacts selectively with a transferrin homolog found in alcoholics, wherein said alcoholics are individuals who ingest 60 grams of more of ethanol per day for a period of one week or more, but not found in non-alcoholics, wherein said non-alcoholics are individuals who do not ingest 60 grams or more of ethanol per day for a period of one week or more, and wherein said homolog lacks an amount of carbohydrate chain normally attached to Asn 413 and/or Asn 611 in a transferrin molecule, said amount sufficient to expose an epitope within about 14 amino acid residues of Asn 413 and/or Asn 611 that is not exposed in said non-alcoholics and is not accessible to the antibody in said non-alcoholics.

10. A hybridoma which produces a monoclonal antibody which reacts selectively with a transferrin homolog lacking an amount of oligosaccharide chain normally attached to transferrin at positions Asn 413 and/or Asn 611, said amount sufficient to expose an epitope on the transferrin homolog within about 14 amino acid residues of Asn 413 and/or Asn 611 that is not exposed in non-alcoholic transferrin and is selectively bound by the antibody in alcoholics but is not by the antibody in non-alcoholics.

11. The hybridoma according to claim 10 prepared by by fusing mouse myeloma cells with spleen cells from a mouse immunized with one or both of the following two peptides, each peptide conjugated to an immunogenic carrier:

Val Leu Ala Glu Asn Tyr Asn Lys Ser Asp Asn Cys Glu
                5                        10
[SEQ ID NO: 1]
and
Gln His Leu Phe Gly Ser Asn Val Thr Asp Cys Ser Gly
                5                        10
[SEQ ID NO: 2].

12. The hybridoma according to claim 11 which produces an IgM class monoclonal antibody.

13. A method of making an antibody which reacts selectively with a transferrin homolog found in alcoholics, wherein said alcoholics are individuals who ingest 60 grams of more of ethanol per day for a period of one week or more, but not found in non-alcoholics, wherein said non-alcoholics are individuals who do not ingest 60 grams or more of ethanol per day for a period of one week or more, the method comprising immunizing an animal with an immunogen comprising the transferrin homolog, and wherein said homolog lacks an amount of carbohydrate chain normally attached to Asn 413 and/or Asn 611 in a transferrin molecule, said amount sufficient to expose an epitope within about 14 amino acid residues of Asn 413 and/or Asn 611 that is not exposed in said non-alcoholics and is not accessible to the antibody in said non-alcoholics.

14. A method of making an antibody which reacts selectively with a transferrin homolog lacking an amount of oligosaccharide chain normally attached to transferrin at positions Asn 413 and/or Asn 611, said amount sufficient to expose an epitope on the transferrin homolog within about 14 amino acid residues of Asn 413 and/or Asn 611 that is not exposed in non-alcoholic transferrin and is selectively bound by the antibody in alcoholics but is not by the antibody in non-alcoholics, the method comprising immunizing an animal with an immunogen comprising the transferrin homolog, or a portion thereof comprising said exposed epitope.

15. The method of claim 14 wherein the animal is immunized with one or both of the following two peptides, each peptide conjugated to an immunogenic career:

Val Leu Ala Glu Asn Tyr Asn Lys Ser Asp Asn Cys Glu
                5                        10
[SEQ ID NO: 1]
and
Gln His Leu Phe Gly Ser Asn Val Thr Asp Cys Ser Gly
                5                        10
[SEQ ID NO: 2].

16. A method of making a monoclonal antibody which reacts selectively with a transferrin homolog found in alcoholics, wherein said alcoholics are individuals who ingest 60 grams of more of ethanol per day for a period of one week or more, but not found in non-alcoholics, wherein said non-alcoholics are individuals who do not ingest 60 grams or more of ethanol per day for a period of one week or more, wherein said homolog lacks an amount of carbohydrate chain normally attached to Asn 413 and/or Asn 611 in a transferrin molecule, said amount sufficient to expose an epitope within about 14 amino acid residues of Asn 413 and/or Asn 611 that is not exposed in said non-alcoholics, the method comprising:

a) immunizing a mouse with an immunogen comprising the transferrin homolog or a portion thereof comprising said exposed epitope;

b) fusing immunoglobulin-producing cells from the immunized mouse with mouse myeloma cells; and c) selecting hybridomas that produce the antibody that reacts selectively with said exposed epitope in the transferrin homolog.

17. The method of claim 16 further comprising:

d) culturing the selected hybridoma cells in culture medium; and e) recovering the antibody from the culture medium.

18. The method of claim 16 further comprising:

d) injecting the selected hybridoma cells into a mouse so as to cause the formation of an ascites-producing tumor; and e) recovering the antibody from the ascites.

19. A method of making a monoclonal antibody which reacts selectively with a transferrin homolog lacking an amount of oligosaccharide chain normally attached to transferrin at positions Asn 413 and/or Asn 611, said amount sufficient to expose an epitope on the transferrin homolog within about 14 amino acid residues of Asn 413 and/or Asn 611 that is not exposed in non-alcoholic transferrin and is selectively bound by the antibody in alcoholics but is not by the antibody in non-alcoholics, the method comprising:
   a) immunizing a mouse with an immunogen comprising the transferrin homolog or a portion thereof comprising said exposed epitope;
   b) fusing immunoglobulin-producing cells from the immunized mouse with mouse myeloma cells; and
   c) selecting hybridomas that produce the antibody that reacts selectively with said exposed epitope in the transferrin homolog.

20. The method of claim 19 further comprising:
   d) culturing the selected hybridoma cells in culture medium; and
   e) recovering the antibody from the culture medium.

21. The method of claim 19 further comprising:
   d) injecting the selected hybridoma cells into a mouse so as to cause the formation of an ascites-producing tumor; and
   e) recovering the antibody from the ascites.

22. The method of claim 19 wherein the mouse is immunized with one or both of the following two peptides, each peptide conjugated to an immunogenic carrier:

Val Leu Ala Glu Asn Tyr Asn Lys Ser Asp Asn Cys Glu
              5                           10
   [SEQ ID NO: 1]

and

Gln His Leu Phe Gly Ser Asn Val Thr Asp Cys Ser Gly
              5                           10
   [SEQ ID NO: 2].

23. The method of claim 22 wherein the immunoglobulin-producing cells are spleen cells.

24. The method of claim 23 wherein the hybridoma produces an IgM class monoclonal antibody.

25. An immunoassay for determining a transferrin homolog found in an alcoholic comprising:
   providing a sample of a body fluid containing transferrin;
   contacting the sample with an antibody which reacts selectively with said transferrin homolog wherein said homolog lacks an amount of carbohydrate chain normally attached to Asn 413 and/or Asn 611 in a transferrin molecule, said amount sufficient to expose an epitope within about 14 amino acid residues of Asn 413 and/or Asn 611 that is not exposed in non-alcoholic transferrin and is not selectively bound by the antibody in a non-alcoholic, wherein said alcoholic is an individual who ingests 60 grams of more of ethanol per day for a period of one week or more, and said non-alcoholic is an individual who does not ingest 60 grams or more of ethanol per day for a period of one week or more;
   determining whether any selective binding complexes are formed between the antibody and any said transferrin homolog in the sample; and
   determining the presence and quantity of the transferrin homolog in the sample from the amount of selective binding complexes formed.

26. An immunoassay for determining a transferrin homolog found in alcoholics comprising:
   providing a sample of a body fluid containing transferrin;
   contacting the sample with an antibody which reacts selectively with said transferrin homology, said homolog lacking an amount of oligosaccharide chain normally attached to transferrin at Asn 413 and Asn 611, said amount sufficient to expose an epitope within about 14 amino acid residues of Asn 413 and/or Asn 611 that is not exposed in non-alcoholic transferrin and is selectively bound by the antibody in alcoholics but is not by the antibody in non-alcoholics, wherein said alcoholics are individuals who ingest 60 grams or more of ethanol per day for a period of one week or more and said non-alcoholics are individuals who do not ingest 60 grams or more of ethanol per day for a period of one week or more;
   determining whether any selective binding complexes are formed between the antibody and any said transferrin homolog in the sample; and
   determining the presence and quantity of the transferrin homolog in the sample from the amount of selective binding complexes formed.

27. A kit for performing an immunoassay comprising a container of an antibody which reacts selectively with a transferrin homolog found in alcoholics, wherein said alcoholics are individuals who ingest 60 grams or more of ethanol per day for a period of one week or more, but not found in non-alcoholics, wherein said non-alcoholics are individuals who do not ingest 60 grams or more of ethanol per day for a period of one week or more, and wherein said homolog lacks an amount of carbohydrate chain normally attached to Asn 413 and/or Asn 611 in a transferrin molecule, said amount sufficient to expose an epitope within about 14 ammo acid residues of Asn 413 and/or Asn 611 that is not exposed in said non-alcoholics and is not selectively bound by the antibody in said non-alcoholics.

28. A kit for performing an immunoassay comprising a container of an antibody reacts selectively with a transferrin homolog lacking an amount of oligosaccharide chain normally attached to transferrin at positions Asn 413 and/or Asn 611, said amount sufficient to expose an epitope on the transferrin homolog within about 14 amino acid residues of Asn 413 and/or Asn 611 that is not exposed in non-alcoholic transferrin and is selectively bound by the antibody in alcoholics but is not by the antibody in non-alcoholics.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 13 amino acids
( B ) TYPE: amino acid
( C ) STRANDEDNESS:
( D ) TOPOLOGY: linear ( x i ) SEQUENCE DESCRIPTION:SEQ ID NO:1:

Val Leu Ala Glu Asn Tyr Asn Lys Ser Asp Asn Cys Glu
                    5                   10

( 2 ) INFORMATION FOR SEQ ID NO:2:

( i ) SEQUENCE CHARACTERISTICS:
( A ) LENGTH: 13 amino acids
( B ) TYPE: amino acid
( C ) STRANDEDNESS:
( D ) TOPOLOGY: linear ( x i ) SEQUENCE DESCRIPTION:SEQ ID NO:2:

Gln His Leu Phe Gly Ser Asn Val Thr Asp Cys Ser Gly
                    5                   10